US00PP14841P2

(12) United States Plant Patent
Apps

(10) Patent No.: US PP14,841 P2
(45) Date of Patent: Jun. 1, 2004

(54) DAYLILY PLANT NAMED 'JUST PLUM HAPPY'

(50) Latin Name: *Hemerocallis hybrida*
Varietal Denomination: Just Plum Happy

(75) Inventor: Darrel A. Apps, Bridgeton, NJ (US)

(73) Assignee: Centerton Nursery, Inc., Bridgeton, NJ (US)

( * ) Notice: Subject to any disclaimer, the term of this patent is extended or adjusted under 35 U.S.C. 154(b) by 0 days.

(21) Appl. No.: 10/661,639

(22) Filed: Sep. 15, 2003

(51) Int. Cl.[7] ..... A01H 5/00
(52) U.S. Cl. ..... Plt./312

(58) Field of Search ..... Plt./312

*Primary Examiner*—Kent Bell
(74) *Attorney, Agent, or Firm*—Burns, Doane, Swecker & Mathis, L.L.P.

(57) ABSTRACT

A new and distinct Hemerocallis cultivar of the dormant type named 'Just Plum Happy' is provided. The new cultivar is very floriferous and forms attractive multi-colored blossoms over an extended period of time that commonly beings during mid- to late-June and commonly ends during mid-October in U.S.D.A. Hardiness Zone No. 6. The blossoms are bright flesh pink with a dark purple eye and a picotee edge. The new plant readily forms fans and readily forms a number of scapes per fan. The new cultivar is particularly well suited for growing as distinctive colorful ornamentation in the landscape.

2 Drawing Sheets

Botanical/commercial classification: *Hemerocallis hybrida*/Daylily.
Varietal denomination: cv. 'Just Plum Happy'.

SUMMARY OF THE INVENTION

The present invention comprises a new and distinct cultivar of Hemerocallis of the dormant type, and hereinafter is referred to by the cultivar name 'Just Plum Happy'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during July, 1995, at Bridgeton, N.J., U.S.A. The female parent (i.e., the seed parent) of the new cultivar was the 'Strawberry Candy' cultivar (non-patented in the United States) having strawberry-pink flowers which display a diameter of approximately 10 cm and less than optimum substance.

The male parent (i.e., the pollen parent) of the new cultivar was the 'Heady Wine' cultivar (non-patented in the United States) having cream with a wine-colored eye zone flowers which display a diameter of approximately 12.5 cm and less than optimum substance. Each parent is registered with the American Hemerocallis Society.

The parentage of the new cultivar can be summarized as follows:

'Strawberry Candy'×'Heady Wine'.

The seeds resulting from the above pollination were sown and small plantlets were obtained which were physically and biologically different from each other. A number of such plants were transplanted into the field at Bridgeton, N.J., U.S.A. during July, 1996. Selective study during August, 1997 resulted in the identification of a single plant of the new cultivar.

It was found that the new Hemerocallis cultivar of the present invention is of the dormant type and possesses the following combination of characteristics:

(a) forms attractive bright flesh pink flowers with a dark purple eye and a picotee edge having substantial substance and a recurved funnel form, (b) possesses a long blooming season with multiple repeat blooming, (c) exhibits a propensity to readily display a plurality of fans, and (d) readily forms a plurality of scapes per fan over the flowering season.

The Hemerocallis×'Just Plum Happy' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season of up to approximately 90 days in U.S.D.A. Hardiness Zone No. 6. This blooming characteristic sometimes is termed multiple-repeat blooming. Such blooming commonly begins in mid- to late-June and commonly ends during mid-October. This compares to a bloom period of less than about 30 days for over 99 percent of the hybrid Daylilies presently available in the trade.

As indicated, the Hemerocallis×'Just Plum Happy' cultivar exhibits attractive multi-colored flowers that readily can be distinguished from the orange-yellow flowers of the 'Stella D' Oro' cultivar and the medium yellow flowers of the Hemerocallis×'Happy Returns' cultivar. To the best of the knowledge of the originator, the 'Just Plum Happy' cultivar is the first long and substantially continuously blooming Daylily having flowers that exhibit a flesh pink coloration with a dark purple eye and a picotee edge hue.

The new cultivar can form up to 5 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on May 10, 1998 at Bridgeton, N.J., U.S.A. At the time of such asexual reproduction, the original plant of the new cultivar consisted of a clump of five fans that were phenotypically identical to each other. More specifically, the clump of the new cultivar was removed from the field and the fans were divided. It has been demonstrated that the characteristics of the new cultivar are firmly fixed and are well retained following this asexual reproduction.

Hemerocallis×'Just Plum Happy' has not been observed under all possible environmental conditions to date. Accordingly, it is possible that the phenotype may vary somewhat with variations in the environment, such as temperature, light, day length, contact with pesticides, etc.

The new cultivar is being marketed beginning in June 2003 while bearing the United States registered HAPPY EVER APPSTER trademark.

BRIEF DESCRIPTION OF THE PHOTOGRAPHS

The accompanying photographs were prepared during June, 2003, and show as nearly true as it is reasonably possible to make the same in color illustrations of this character, the original plant and flowers of the new cultivar of the present invention. The plant was being grown outdoors in a pot at Bridgeton, N.J., U.S.A.

DETAILED DESCRIPTION

The chart used in the identification of colors described herein is The R.H.S. Colour Chart of The Royal Horticultural Society, London, England. In some instances, more common color terms are provided and are to be accorded their usual dictionary significance. The original plant of the new cultivar is described when observed during August 1997,when approximately one year of age while growing at Bridgeton, N.J., U.S.A. under field growing conditions.

Plant:

*Height.*—Approximately 40 cm at an age of one year.

*Width.*—Approximately 92 cm at an age of one year.

Figure 2:
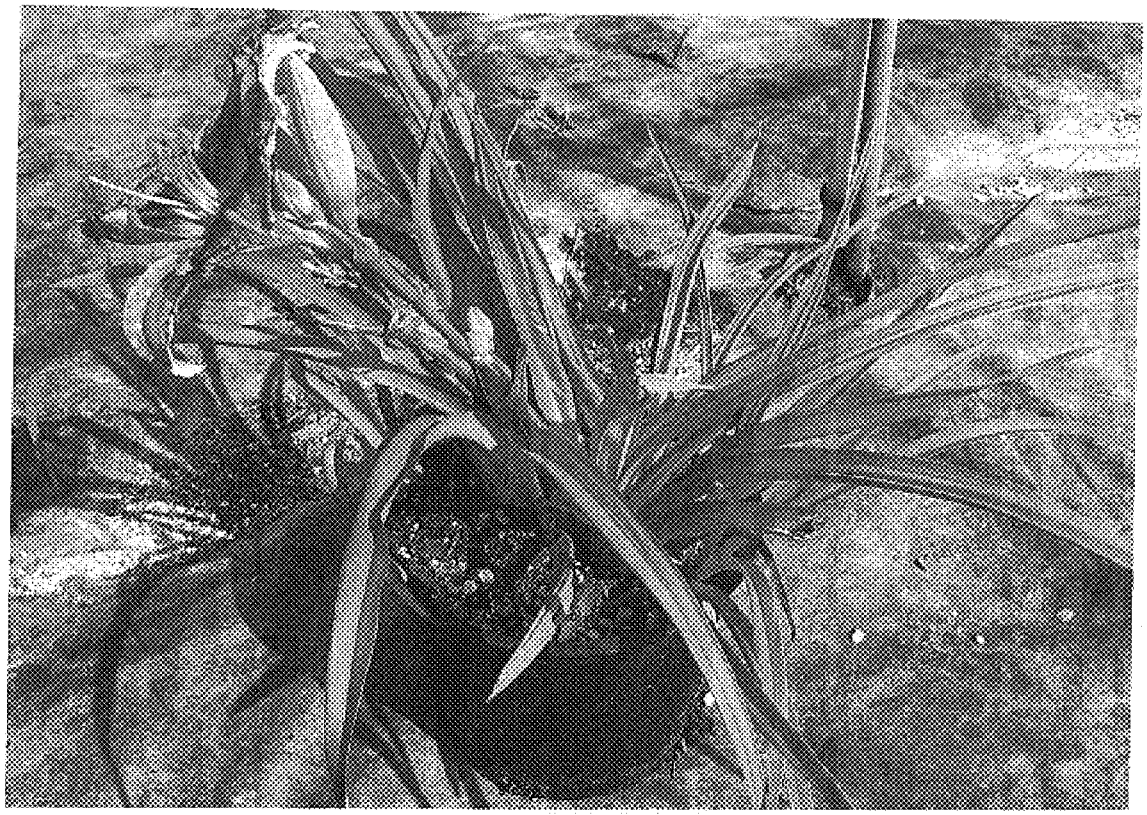
FIG. 2 shows an overall view of the plant while flowering.

*Foliage.*—Form: single stem, substantially erect shape from a fan-shaped base having narrow arching, long, keeled, grass-like glabrous slightly-textured leaves that are two-ranked at the base of the scape. Quantity: abundant, with a mature plant commonly having approximately 18 leaves per fan. Leaf Size: commonly approximately 3.5 cm in width on average and approximately 46 cm in length on average. Leaf Shape: linear and long-keeled (as illustrated in FIG. 2) with entire margins. Texture: glabrous and ridged. Color: Green Group 137A on both surfaces. Type: dormant with the leaves deciduating during the winter in U.S.D.A. Hardiness Zone No. 6b.

*Scape.*—Color: Green Group 137C. Length: commonly approximately 34 cm on average.

*Disease resistance.*—Typical of Hemerocallis with no problems having been observed to date.

Figure 1:
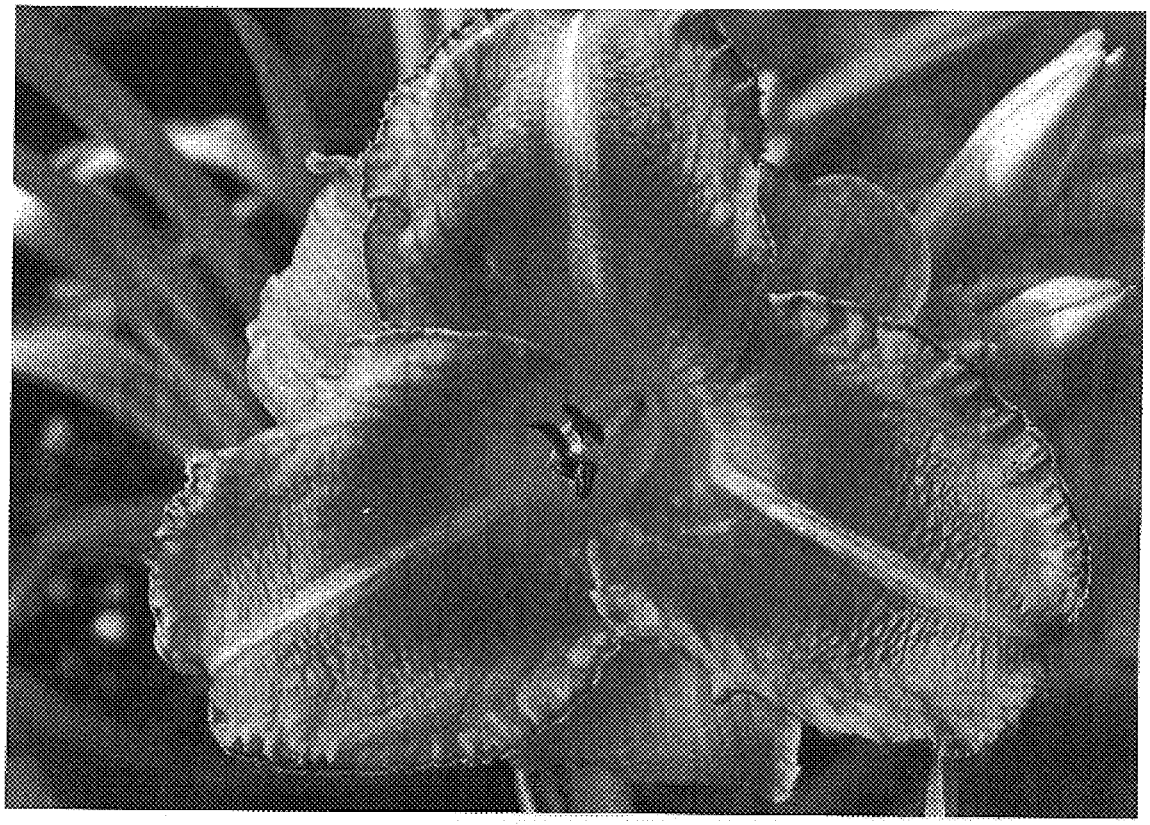
FIG. 1 shows a close view of a typical flower and buds of the new Hemerocallis×'Just Plum Happy' cultivar. The attractive multi-coloration and configuration of the blossoms are illustrated.

Inflorescence:

*Bud.*—Form: modified oblanceolate (as illustrated in FIGS. 1 and 2). Size: on the day prior to opening commonly approximately 9 cm in length on average and approximately 3 cm in width on average. Color: Yellow Group 8B. Opening Rate: commonly approximately three hours on average. Peduncle Character: rigid and sturdy. Peduncle Color: Yellow-Green Group 151B.

*Flower.*—Size: commonly has a diameter of approximately 11 cm on average and a depth of approximately 7 cm on average. Borne: singly on the branchlets of a sturdy erect rachis which is ramulose. Each scape commonly has at least twelve peduncles, each of which divides into approximately three pedicels. Blooms Per Scape: Commonly ranges from 1 to 2 each day. Tepalage: each flower consists of six perianth segments wherein there are three outer tepals and three inner tepals all in an imbricated arrangement. Outer Tepal Shape: oblanceolate with slightly undulated entire margins and an acuminate apex. Outer Tepal Texture: slightly ribbed. Outer Tepal Size: commonly approximately 8 cm in length on average and approximately 3.5 cm in width on average. Outer Tepal Color: Greyed-Orange Group 170C with a chevron on Greyed-Red Group 180D. Inner Tepal Texture: corrugated with a central rib. Inner Tepal Size: commonly approximately 9 cm in length on average and approximately 5.5 cm in width on average. Inner Tepal Color: Yellow Group 13A at the base, Greyed-Orange Group 170C overall, and an eye zone of Red-Purple Group 61A with a watermark of Orange-Red Group 180C. Blooming Habit: the flowers commonly bloom substantially continuously and the scape commonly is substantially continuously in bloom for up to approximately 90 days per year in U.S.D.A. Hardiness Zone No. 6. Effects of Weather: the flowers well withstand rain damage in view of the strength of the tepals. Lasting Quality: commonly at least 16 hours. As with other Hemerocallis cultivars, the flower color eventually fades somewhat during the day with the natural effects of environmental conditions and ongoing maturity. Fragrance: none.

*Reproductive organs.*—Stamen Number: six per flower. Stamen Disposition: individually inserted at the summit of the perianth tube. Anther Disposition: introrse. Anther Size: approximately 9 mm in length. Anther Color: Violet-Blue Group 95B with an edge of Black Group 202A. Filament Configuration: slender. Filament Length: commonly approximately 5.5 cm on average. Filament Color: Yellow Group 13A. Pollen Color: Yellow-Orange Group 17A. Pistil Number: one per flower. Style Length: approximately 7 cm in length on average. Style Color: Greyed-Orange Group 170C. Stigma Color: Yellow Group 13B. Ovaries: three-celled, oblong, and becoming a loculiedally three-valved capsule.

*Fruit.*—Configuration: the seed pod is in the form of an ovoid capsule. Color: at maturity commonly is near Green Group 137A. Fertility: the seeds are fertile.

Hardiness:

*Cold tolerance.*—U.S.D.A. Hardiness Zone No. 5a.

*Heat tolerance.*—U.S.D.A. Hardiness Zone No. 8b.

I claim:

1. A new and distinct cultivar of Hemerocallis plant having the following combination of characteristics:

(a) forms attractive bright flesh pink flowers with a dark purple eye and a picotee edge having substantial substance and a recurved funnel form, (b) possesses a long blooming season with multiple repeat blooming, (c) exhibits a propensity to readily display a plurality of fans, and (d) readily forms a plurality of scapes per fan over the flowering season;

substantially as illustrated and described.

* * * * *